(12) United States Patent
Eisele et al.

(10) Patent No.: US 6,645,360 B1
(45) Date of Patent: Nov. 11, 2003

(54) PLANAR SENSOR ELEMENT FOR A GAS SENSOR

(75) Inventors: Ulrich Eisele, Stuttgart (DE); Lothar Diehl, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 37 days.

(21) Appl. No.: 09/763,344

(22) PCT Filed: Jun. 16, 2000

(86) PCT No.: PCT/DE00/01907

§ 371 (c)(1),
(2), (4) Date: Apr. 20, 2001

(87) PCT Pub. No.: WO00/79259

PCT Pub. Date: Dec. 28, 2000

(30) Foreign Application Priority Data

Jun. 19, 1999 (DE) ........................................ 199 28 165

(51) Int. Cl.$^7$ ............................................. G01N 27/407
(52) U.S. Cl. ......................... 204/426; 204/408; 204/427
(58) Field of Search ................................ 204/421–429, 204/408

(56) References Cited

U.S. PATENT DOCUMENTS

| 5,144,249 | A | | 9/1992 | Kurishita et al. |
| 5,429,737 | A | | 7/1995 | Pribat et al. |
| 5,444,249 | A | | 8/1995 | Wong |
| 5,529,677 | A | * | 6/1996 | Schneider et al. |

FOREIGN PATENT DOCUMENTS

| DE | 197 13 904 | 10/1998 |
| DE | 197 46 516 | 5/1999 |
| DE | 198 15 174 | 10/1999 |

* cited by examiner

Primary Examiner—T. Tung
(74) Attorney, Agent, or Firm—Kenyon & Kenyon

(57) ABSTRACT

A sensor element, having a ceramic body made of a laminate having at least one ceramic foil and having a heating element embedded in the ceramic body. At least the longitudinal edges of the ceramic body have a chamfer. The heat source formed by the heating element lies in the direction of the bisector of an angle which is enclosed by a chamfer's edge lying closest to the heating element. The chamfer is formed in such a way that the angle enclosed by the large surface side edge, is larger than an angle enclosed by a narrow side edge.

1 Claim, 3 Drawing Sheets

PLANAR SENSOR ELEMENT FOR A GAS SENSOR

The present invention relates to a sensor element for a gas sensor, especially for determining the concentration of gas components in gas mixtures.

BACKGROUND INFORMATION

Platelet-shaped ceramic sensor elements, which are produced by sintering at least one ceramic solid electrolyte foil provided with functional layers, are used, for instance, as lambda probes for determining the oxygen content in the exhaust gases of internal combustion engines. The solid electrolyte foils of these sensor elements are oxygen ion-conducting, and are printed in the unsintered condition with functional layers (electrodes, circuit-board conductors, heating conductors and the like), laminated together to a green body and then sintered at a temperature of 1400° C., for example.

Instead of a laminate of ceramic solid electrolyte foils, solid electrolyte layers can also be used, which are printed one over the other in individual printing steps, together with the functional layers onto a supporting substrate, The named sensor elements are exposed to the hot exhaust gas stream of the internal combustion engine, which has various temperatures. Because of the temperature changes in the exhaust gas stream, which occur suddenly and with various intensities, the sensor elements experience thermal shock, resulting in mechanical tension in the surface area, especially at the edges of the sensor elements.

To raise the shock resistance of the sensor elements, it is known from U.S. Pat. No. 5,144,249 to break the longitudinal edges, i.e., to provide each with a chamfer, the chamfer being applied at an angle of about 45 degrees. The application of the chamfers is performed with a grinding procedure on the already sintered sensor element.

Investigations have revealed that, in spite of the chamfer, during heating of the sensor element, stress cracks still occur. A condition of maximum tensile stress in the chamfer appears as soon as a few seconds after switching on the heating element integrated into the sensor element. During this, the stress cracks start especially from the large surface side edge of the chamfer, and appear particularly when abrupt cooling of the surface of the sensor element occurs because water from condensation impinges on it.

The present invention is based on the object of further improving the shock resistance of planar, ceramic sensor elements.

SUMMARY OF THE INVENTION

The sensor element according to the present invention, has the advantage that the thermal shock resistance of the planar sensor element is improved. It could be determined that, especially at the critical edge of the chamfer lying nearest to the heat source, stress cracks no longer appear.

In consideration of the varying heat conducting capabilities of the heating conductor made of platinum-cermet, of the insulating layers made of $Al_2O_3$ for the heating conductor and of the solid electrolyte foil made of stabilized $ZrO_2$, an edge geometry was found for the sensor element, which realizes a substantially uniform warming of the large surface side edge lying closest to the heat source, and thereby a symmetrical tension condition is generated at this edge of the chamfer. The edge geometry takes into account the various heat conducting capabilities of platinum, or rather Pt-cermet of ca. 70 W/Km, of $Al_2O_3$ insulating layers of ca. 10 W/Km and of $ZrO_2$ foil of ca. 5 W/Km. It was also found that lesser tension conditions occur at a blunt chamfer. In this connection, the edge of the chamfer lying closest to the heat source was selected as more blunt, meaning that this edge forms a larger angle.

Advantageous further developments of the sensor element according to the present invention come to light. The large contact surface of the heating element relative to the large surface of the heater foil involves a large heating current. Therefore it becomes expedient to select the width of the sealing frame larger than the thickness of the heater foil. Thus, additionally, the distance of the surface of the chamfer from the heating conductor is increased even with a flat chamfer in relation to the large area of the heater foil, a distance as large as possible from the heating conductor, for insulating the heating conductor, is realized. A heater foil as thick as possible also guarantees that the critical edge on the large area side of the chamfer lies farther away from the heating element. Because of the lesser deflection of the sensor element resulting from this, lower tensile stresses develop.

It further turned out expedient to form a multiple chamfer, particularly a double chamfer at the edge of the sensor element, with the flat chamfer at the large area of the sensor element running out to a steeper chamfer on the narrow side. It also turned out that edgy transitions between the surfaces should be avoided by rounding off the edges. In order to avoid cracks at the edges of the front face, it is further advantageous to furnish the edges at the front face, too, with appropriate chamfers, and here too, it is especially advantageous to form the sealing frame at the front face wider than the thickness of the heater foil.

BRIEF DESCRIPTION OF THE DRAWINGS

FIGS. 1 and 2 show a sensor element used as a so-called lambda sensor for ascertaining the oxygen content in exhaust gases of internal combustion engines in motor vehicles or in furnaces. The sensor element has an essentially long-extending, platelet-shaped ceramic body 10, having an end section 12 on the side of the gas to be measured and an end section on the terminal side which is not illustrated in greater detail (FIG. 2).

Figure 1:
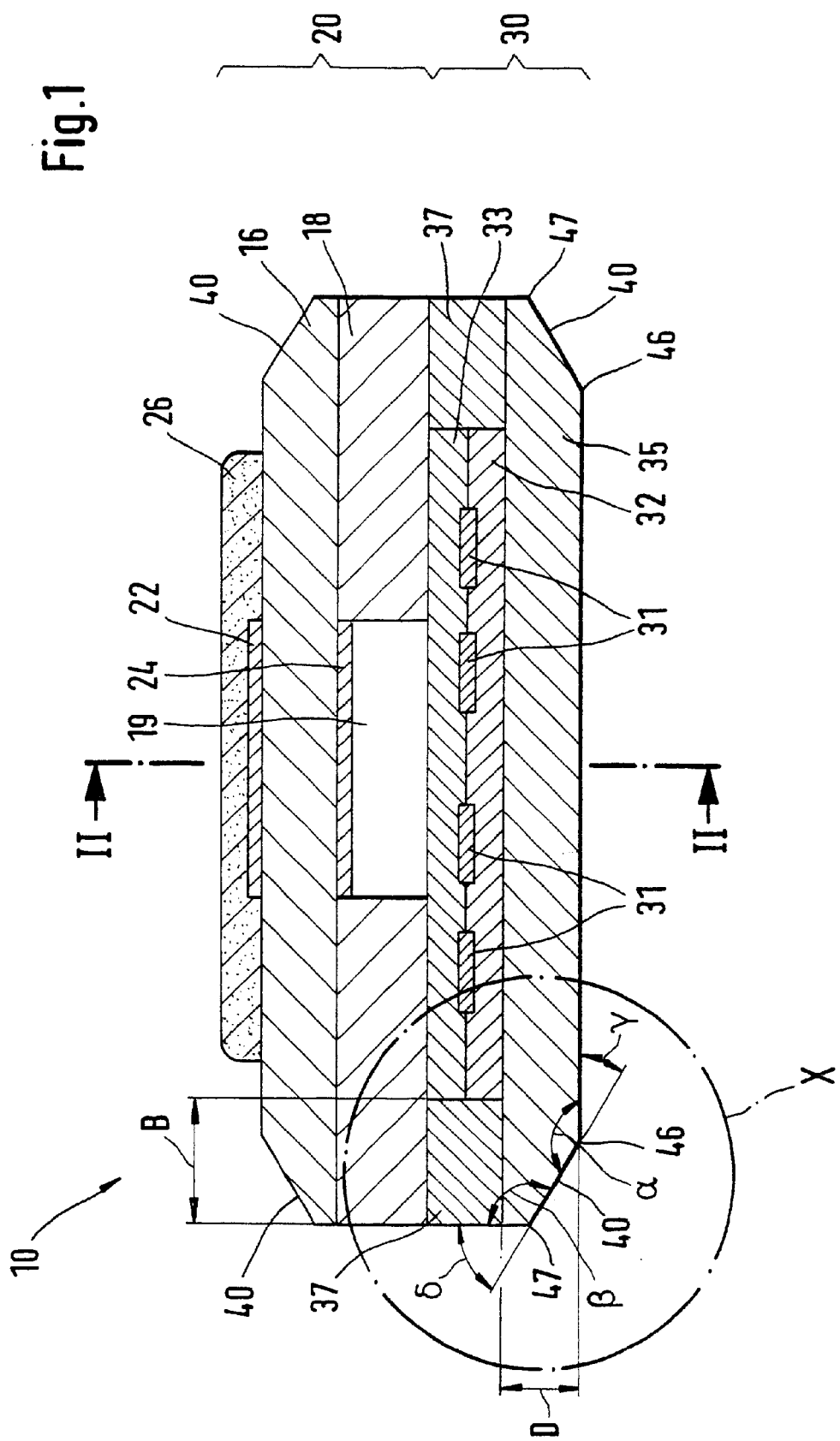
FIG. 1 shows a cross-section through a sensor element according to the present invention.

As the sectional view in FIG. 1 makes clear, the sensor element is designed with a measuring cell 20 and a heating element 30. The measuring cell 20 in the present exemplary embodiment is a so-called Nernst cell, having a first solid electrolyte foil 16 as well as a second solid electrolyte foil 18, a reference gas duct 19 being integrated into the second solid electrolyte foil 18. Reference gas duct 19 is closed at end section 12 on the side of the measuring gas, and is furnished with an opening, not illustrated, at the end section on the terminal side.

At end section 12 on the side of the measuring gas, measuring cell 20 has a measuring electrode 22 and a reference electrode 24 pointing into reference gas duct 19. Air as reference atmosphere is conducted to reference electrode 24 via reference gas duct 19. Measuring electrode 22 is covered with a porous protective layer 26 and exposed to the measuring gas.

Heating element 30 has a heating conductor 31, which is embedded between a first electrical insulating layer 32 and a second electrical insulating layer 33, the insulating layers 32, 33 being made of $Al_2O_3$. Insulating layer 32 is printed onto a third solid electrolyte foil 35, which is denoted as heating foil. Heating foil 35 forms a covering foil for heating element 30, toward the outside. The solid electrolyte foils 16, 18, as well as heating foil 35 are made, for example, of stabilized $ZrO_2$, and therefore they are oxygen ion-conducting.

Insulating layers 32, 33, which are designed to be porous, are enclosed by a gas-tight foil frame 37, foil frame 37 being preferably made of the material of the adjacent solid electrolyte foils 18, 35.

To produce the sensor element, solid electrolyte foils 16, 18 of measuring cell 20, having electrodes 22, 24, and the circuit-board conductors not more closely designated, printed on them, are laminated, together with heating foil 35 of heating element 30, heating foil 35 being furnished with insulating layers 32, 33, heating element 31 and foil frame 37, to the platelet-shaped ceramic body 10, and are sintered.

In their original condition, the individual solid electrolyte foils 16, 18, 35 have sharp edges, so that after the laminating together of solid electrolyte foils 16, 18, 35, ceramic body 10 has an essentially rectangular cross-section with sharp edges.

Figure 2:
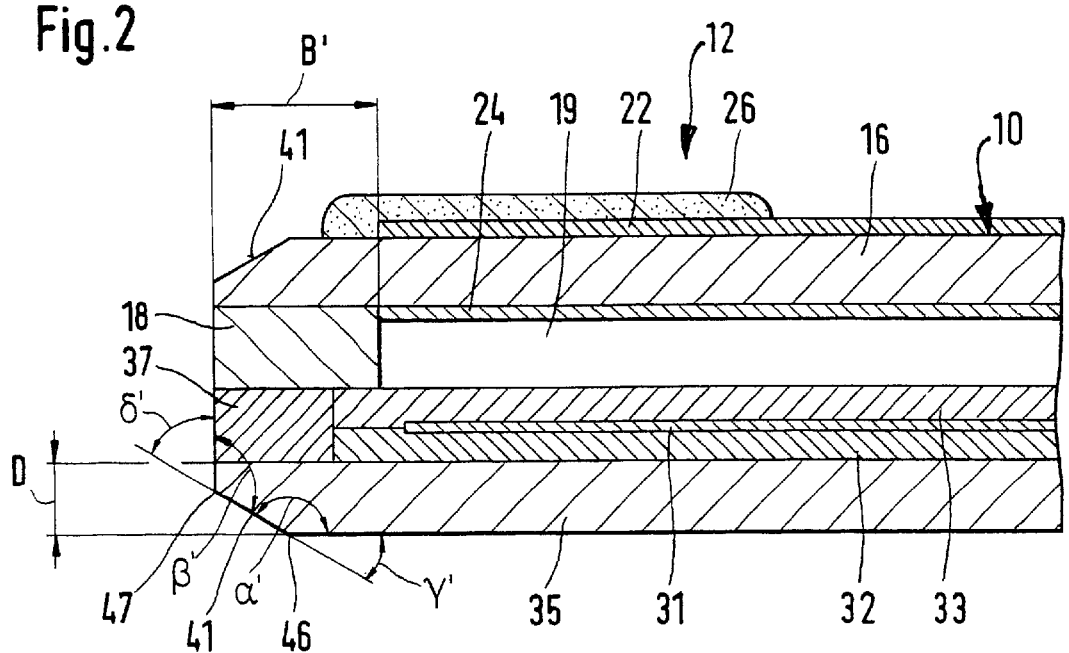
FIG. 2 shows a longitudinal section along line II—II in FIG. 1.

According to FIG. 2, a further embodiment also provides a further chamfer 41 at the four edges of at least the front face of end section 12 on the side of the measuring gas. In addition to that, a chamfer can also be provided on the edges of the front face of the end section on the connecting side. It is advisable to form the geometry of chamfers 40, on the longitudinal edges, and of chamfers 41, on the edges of the front face, in the same way.

Chamfers 40, 41 can have the geometry of the specific embodiments illustrated in FIGS. 1 to 5.

The chamfers 40, illustrated in FIG. 1, each have an edge 46 on the large surface side and an edge 47 on the narrow surface side, and form an angle α at the large area side edges 46 and an angle β at the narrow area side. In this connection, angle α, formed at the large area side edge 46 is greater than the angle β formed at the narrow side edge 47. In the present exemplary embodiment, angle α was picked to be 150 degrees, which then makes angle β 120 degrees. Complementary angle γ, which is 30 degrees if angle α is 150 degrees, and complementary angle δ, which is 60 degrees if angle β is 120 degrees, are given as measuring angles.

In order to form the edge of chamfer 40, on the large area side, as far as possible away from heating conductors 31 or insulating layers 32, 33, the width B of sealing frame 37 is greater than thickness D of heating foil 35. In order to increase the distance of the critical, large area side edges 46 of chamfers 40, 41 from the heat source, and to remove the additional tensile stress caused by the asymmetry of heating, it is also possible to choose heating foil 35 thicker than at least one of the other foils 16, 18, and/or to choose thickness D of heating foil 35 to be greater than width B of foil frame 37.

Chamfers 41, provided, as seen in FIG. 2, at the end face of end section 12 on the side of the measuring gas, are developed analogously to chamfers 40, the angles α', β' λ' and δ' corresponding to the respective angles α, β, γ and δ. In order to guarantee, here too, that the large area side edge 46 of chamfer 41 extends at a distance from heating conductor 31 or from insulating layers 32, 33, in this case, the width B' of frame 18' on the end face side is made wider than the thickness D of heating foil 35.

Figure 6:
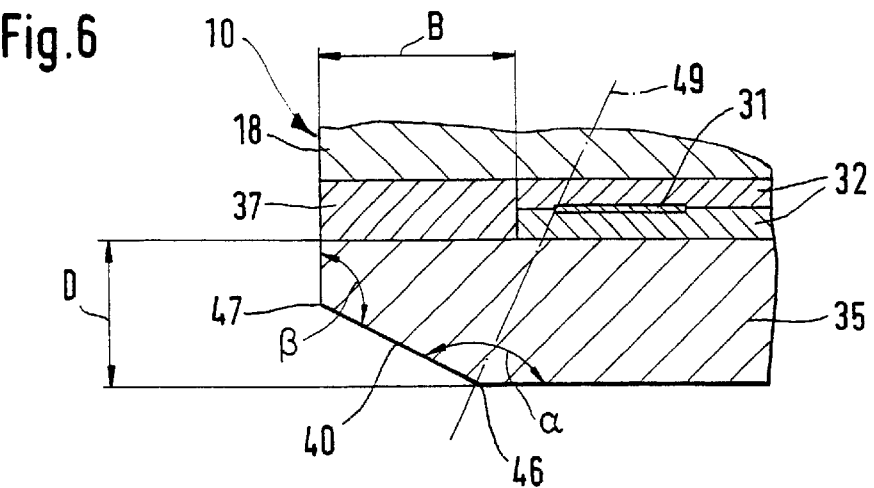
FIG. 6 shows a cutaway portion X in FIG. 1 showing a further refinement of the chamfer of a sensor element according to the present invention.

A further refined sensor element according to the present invention is seen in FIG. 6. In this exemplary embodiment, the thickness D of heating foil 35, the width B of foil frame 37 and/or the position of heating conductor 31 in insulating layers 32, 33 are coordinated in such a way, that the heat source formed by heating conductor 31 lies in the direction of the bisector 49 of angle α, α' which is formed at edge 46 of chamfer 40. Here, edge 46 is the edge lying closest to heating element 30. The position of the heat source is then determined by the position of the outer printed conductor of heating conductor 31. This guarantees that extensively symmetrical warming comes about at the critical edge 46, considering the various heat conducting capabilities of the layer laminate.

Figure 3:
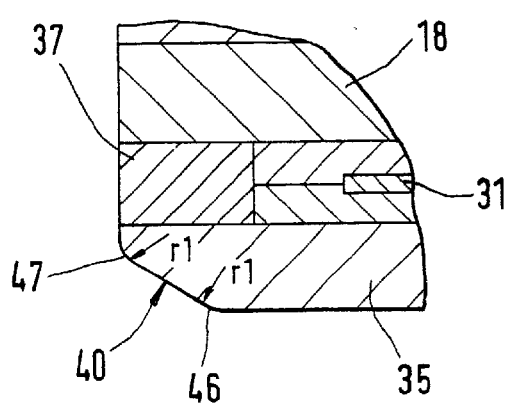
FIG. 3 shows a cutaway portion X in FIG. 1 according to a second embodiment of a chamfer.

An additional possible specific embodiment of the geometry of chamfers 40, 41 is seen in FIG. 3. There, the large surface side edge 46 and the narrow side edge 47 are each rounded off at a radius of $r_1$, of 0.2 to 1.0 mm, for example.

Figure 4:
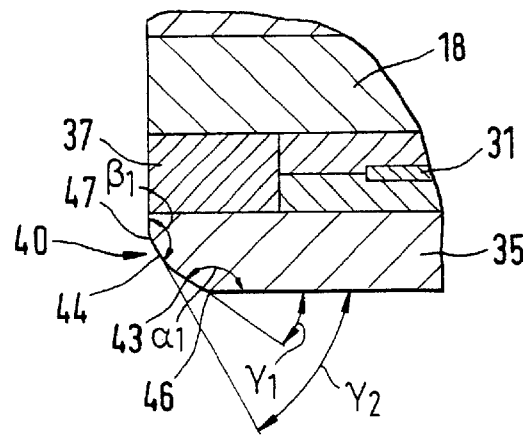
FIG. 4 shows a cutaway portion X in FIG. 1 according to a third embodiment of a chamfer.

One embodiment having a double chamfer is shown in FIG. 4. Here a flat running first chamfer section 43 proceeds at first from the large surface of heating foil 35 at an angle $\gamma^1$ of 30 degrees, for instance, and adjoining this toward the narrow side, a second chamfer section 44 is formed at an angle $\gamma_2$ of 60 degrees, for instance. The enclosed angles $\alpha_1$ and $\beta^1$ are then each 150 degrees.

Figure 5:
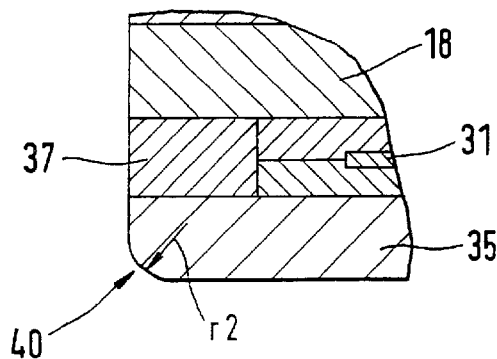
FIG. 5 shows a cutaway portion X in FIG. 1 according to a fourth embodiment of a chamfer.

Finally, in a specific embodiment as in FIG. 5, chamfer 40 is designed as a round shape with radius $r_2$ of 0.1 to 0.3 mm, for example.

Chamfers 40, 41 can be produced, for example, by grinding the ready-sintered sensor elements. But it is also possible to provide the sensor element, while it is in the green, unsintered condition, with chamfers 40, 41 by shaping. Additional production methods of chamfers 40, 41, for example by laser treatment, are possible.

In order to reduce the formation of cracks on chamfers 40, 41 even further, one possibility is to break the edges 46, 47 of chamfers 40, 41, by affixing radii, for instance, as in the exemplary embodiment in FIG. 3. A further possibility is to break the edges 46, 47 of chamfers 40, 41 using a non-directional process, for instance, by treatment of the sensor element by sandblasting using fine ceramic powder, similar to grit blasting. Breaking the edges is also possible by rounding the edges, especially by fine grinding counter to the direction of the grinding process used in producing chamfers 40, 41.

Finally, a method can be applied for breaking the edges, in which the critical end section 12, on the side of the measuring gas, is dipped into a bath of abrasive particles, e.g. $ZrO_2$ particles, and rotated rapidly. During this process, the axis of rotation preferably coincides with the axis of symmetry of the large surface and thereby the greatest relative motion of the edges of the sensor element is achieved.

What is claimed is:

1. A sensor element, comprising:
   a ceramic body made of a laminate of at least one ceramic foil; and
   a heating element embedded in the ceramic body, wherein:
      at least longitudinal edges of the ceramic body include a chamfer in a vicinity of the heating element, the chamfer includes at least one large surface side edge and at least one narrow side edge, the chamfer is formed as a multiple chamfer including a plurality of chamfer sections, and
      an enclosed angle at the at least one large surface side edge is greater than the enclosed angle at the at least one narrow side edge.

* * * * *